United States Patent [19]
Solomon et al.

[11] Patent Number: 5,853,368
[45] Date of Patent: Dec. 29, 1998

[54] ULTRASOUND IMAGING CATHETER HAVING AN INDEPENDENTLY-CONTROLLABLE TREATMENT STRUCTURE

[75] Inventors: Rodney J. Solomon, Andover; Michael Peszynski, Newburyport; Martin K. Mason, Andover, all of Mass.

[73] Assignee: Hewlett-Packard Company, Palo Alto, Calif.

[21] Appl. No.: 774,129

[22] Filed: Dec. 23, 1996

[51] Int. Cl.⁶ .............................. A61B 8/00; A61N 1/05
[52] U.S. Cl. ............................................ 600/439; 607/122
[58] Field of Search .............................. 128/662.06, 642, 128/662.03, 660.03; 600/439, 462–464, 471; 607/122

[56] References Cited

U.S. PATENT DOCUMENTS

| | | | |
|---|---|---|---|
| 4,651,718 | 3/1987 | Collins et al. | 128/4 |
| 4,763,662 | 8/1988 | Yokoi | 600/464 |
| 4,790,294 | 12/1988 | Allred, III et al. | 128/4 |
| 4,936,281 | 6/1990 | Stasz | 128/660.03 |
| 5,000,185 | 3/1991 | Yock | 128/662.03 |
| 5,109,859 | 5/1992 | Jenkins | 600/439 |
| 5,167,233 | 12/1992 | Eberle et al. | 600/463 |
| 5,178,129 | 1/1993 | Chikama et al. | 128/4 |
| 5,295,484 | 3/1994 | Marcus et al. | 128/660.03 |
| 5,313,943 | 5/1994 | Houser et al. | 128/642 |
| 5,313,949 | 5/1994 | Yock | 128/662.06 |
| 5,325,860 | 7/1994 | Seward et al. | 128/662.06 |
| 5,345,940 | 9/1994 | Seward et al. | 128/662.06 |
| 5,373,849 | 12/1994 | Maroney et al. | 128/662.06 |
| 5,385,148 | 1/1995 | Lesh et al. | 128/662.06 |
| 5,391,199 | 2/1995 | Ben-Haim | 607/122 |
| 5,409,000 | 4/1995 | Imran | 128/642 |
| 5,427,118 | 6/1995 | Nita et al. | 128/772 |
| 5,433,198 | 7/1995 | Desai | 128/642 |
| 5,443,489 | 8/1995 | Ben-Haim | 607/115 |
| 5,447,509 | 9/1995 | Mills et al. | 606/1 |
| 5,471,982 | 12/1995 | Edwards et al. | 128/642 |
| 5,471,988 | 12/1995 | Fujio et al. | 600/439 |
| 5,480,422 | 1/1996 | Ben-Haim | 607/122 |
| 5,588,432 | 12/1996 | Crowley et al. | 600/463 |
| 5,651,366 | 7/1997 | Liang et al. | 600/439 |

*Primary Examiner*—Francis Jaworski

[57] ABSTRACT

A catheter apparatus having a main catheter body with an ultrasound transducer mounted into a side of the catheter body proximate to its distal end providing a field of view from the side of the catheter. Mounted axially on the same side of the catheter body is a independently-controllable treatment structure having a deployable segment with a therapeutic segment proximate with its distal end and having a range of movement along a predetermined path including locations only within the imaging field. The location of the treatment structure's therapeutic segment is determinable relative to the ultrasound transducer, enabling accurate and repeated positioning of the therapeutic segment at a desired location within the imaging field where it can be imaged clearly. The treatment structure bends only at the deployable segment, which includes deflection bands connected to an articulation mechanism in a handle. The deflection bands restrict the deployable segment deflections to cause the therapeutic segment of the treatment structure to travel along a predetermined path to locations that necessarily include locations within the imaging field.

22 Claims, 4 Drawing Sheets

ULTRASOUND IMAGING CATHETER HAVING AN INDEPENDENTLY-CONTROLLABLE TREATMENT STRUCTURE

BACKGROUND OF THE INVENTION

1. Field of the Invention

The present invention relates generally to interventional catheters and, more particularly, to ultrasonic treatment catheters providing ultrasonic imaging.

2. Related Art

Cardiac ablation therapy is a commonly used approach to alter cardiac anatomical or conduction systems. Ablation therapy may be performed by an open surgical cardiac procedure or by percutaneous (closed chest) catheterization. Various conventional cardiac catheters and associated procedures have been developed to perform cardiac ablation therapy. However, there are drawbacks to these approaches which either make them impractical or which limit their ability to provide accurate and immediate imaging information of the ablative device's position, thereby preventing the efficient and accurate performance of the ablation therapy.

One conventional technique used to perform cardiac catheterization ablation therapy includes the use of fluoroscopy to visualize the chambers of the heart. Oftentimes, injectable contrast agents are included to enhance the fluoroscopic images. A drawback to this approach is that the accurate positioning of the catheters during ablation is difficult using the crude fluoroscopic images. In addition, this approach does not provide the clinician with the ability to precisely determine the location of the ablation catheter relative to the endocardium and cardiac structures. As a result the duration of the procedure is often extended, increasing the risk of complications and prolonging the patient's exposure to radiation. Furthermore, the thickness and character of the cardiac structures or tissue is not determinable with this arrangement, making it difficult to determine when the desired amount of tissue has been ablated.

To overcome these drawbacks of fluoroscopic techniques, conventional approaches have incorporated the use of ultrasound to provide detailed imaging of the ablation catheter. Typically, fluoroscopy is initially used to generally position an ultrasonic imaging catheter and a separate ablation catheter in the left or right atrium or ventricle of the heart. Then, ultrasound imaging is used to assist in the control of the ablative device located at the end of the ablation catheter during performance of the ablation therapy. However, it is very difficult to locate the ablation device due to the difficulty in positioning the narrow field of view provided by the ultrasonic imaging catheter. In addition, it is difficult to perform the ablation therapy while keeping the ablation device in the field of view provided by the ultrasound catheter since both catheters have to be continually maneuvered to perform the therapy. The unclear and inconsistent imaging results in uncertainty in the success of the procedure.

One conventional approach for determining the position of the ablative or other therapeutic device in the ultrasonic imaging window is described in U.S. Pat. No. 5,325,860 to Seward et al. Seward discloses a catheter having an ultrasound transducer and channel or port that runs axially along its length. A therapeutic device may be inserted through the treatment channel to deliver it to a position proximate the distal end of the catheter for operation within the field of view provided by the transducer. A drawback to this approach is that it is difficult to maintain the cleanliness of the treatment channel. In addition, for the treatment channel to be sufficiently large to receive therapeutic devices, it must consume a significant portion of the catheter's internal volume. This requirement limits the space available for all other functional elements of the catheter, such as the ultrasound transducer. Thus, the size of the catheter must be increased to accommodate such other functional elements or conversely, the ultrasound transducer and other functional elements must be limited in size.

Another approach to aligning the ablation device with an ultrasound imaging window is described in U.S. Pat. No. 5,325,148 to Lesh et al. The Lesh device includes the use of a catheter with a tissue characterization assembly and an ablation assembly permanently fixed relative to each other in a single structure. A drawback to this approach is that the relative fixed positions of the ablative device and ultrasound transducer are such that the ablative device is not in the field of view provided by the transducer. As a result, the transducer cannot be used to monitor the relative position of the ablative device and anatomical structure or tissue to receive the ablation therapy, and is therefore of little assistance during the performance of the ablation therapy.

In an alternative embodiment of the Lesh device, two separate catheters are used: one having an ultrasound transducer and the other having an ablation electrode. The catheters are inserted either in parallel or through different vessels of the body. A problem with this approach is that, as noted above, it is difficult to locate the ablation catheter in the field of view of the ultrasound transducer, even when additional methods, such as fluoroscopy, are used.

What is needed, therefore, is a catheter apparatus that enables the clinician to quickly and accurately image the ablative or other therapeutic device. The catheter should provide a field of view of both, the therapeutic device and the surrounding anatomical features so that their relative position is determinable. The clinician will then be able to perform the desired therapy with improved speed, accuracy and success.

SUMMARY OF THE INVENTION

The present invention relates to a catheter apparatus having a main catheter body with an ultrasound transducer mounted into a side of the catheter body proximate to its distal end providing a field of view from the side of the catheter. Mounted axially on the same side of the catheter body as the transducer is an independently-controllable treatment structure having a deployable segment with a therapeutic segment at or adjacent to its distal end. The therapeutic segment has a restricted range of motion that necessarily includes locations within the imaging field. This novel arrangement provides an image of the position of the treatment structure's therapeutic segment relative to the surrounding anatomical structures when the segment is deployed at a location within the imaging field.

Specifically, the treatment structure is an elongated member having a non-deployable segment axially secured to the catheter body and a deployable segment that bends in a predetermined manner relative to the field of view. The treatment structure includes deflection bands connected to an articulation mechanism located in a handle connected to the proximal ends of the catheter body and treatment structure. The deflection bands are configured to permit deflections of the treatment structure only at the deployable segment. Thus, when the articulation mechanism is operated to apply tensile control forces to a proximal end of one of the deflection bands, the therapeutic segment of the treatment catheter travels along a predetermined path to one or more of many deployed positions within the imaging field of the transducer. The ultrasound transducer is preferably a combination of linear and phased array sensor elements that generate a substantially planar, trapezoidally-shaped imaging field, providing a field of view which extends across the surface the transducer at a distance immediately adjacent to the transducer, and which extends in both proximal and distal directions in the direction of the elongation of the catheter at distances further from the transducer. Other types of ultrasound transducers providing imaging fields having other volumetric configurations may also be provided by the present invention.

In one aspect, the present invention includes a cardiac imaging and ablation catheter wherein the main catheter body is configured to be positioned within the atrium or ventricle of the heart, and the treatment structure is an ablation support structure having an ablation electrode located at the active segment. In alternative embodiments, the active segment includes more that one ablation electrode. In addition, any type of ablation electrode may be used, such as an ablation electrode that generates direct current (DC), radio frequency (RF) or microwave energy. It may also be, for example, a laser or cryoablation device.

In one embodiment of this aspect, the main catheter body is controlled by one or more conventional articulation mechanisms on the handle at the proximal end of the main catheter body. One articulation mechanism provides two-way horizontal steering of the main catheter body while the other articulation mechanism provides two-way vertical steering. Together, the articulation mechanisms provide four-way control of the main catheter body, including the deployable and non-deployable segments of the treatment structure. Alternatively, the catheter apparatus may have only one or no articulation mechanisms depending on the application. These articulation mechanisms are distinct from the treatment structure articulation mechanism of the present invention which provides two-way steering of the treatment structure alone.

During catheterization, the treatment structure is initially placed in a non-deployed position. In this position, the elongated treatment structure is essentially straight and substantially parallel with the longitudinal axis of the main catheter body. In one embodiment, when in the non-deployed position, the therapeutic segment is immediately adjacent to an imaging lens of the transducer. The stiffness of the structures cause them to remain in fixed relation with each other during catheterization. Thus, a clinician inserts the non-deployed cardiac imaging and ablation catheter into the arterial or venous systems and maneuvers it to the a desired location, such as the left or right atrium or ventricle using the main body articulation mechanisms. Once he catheter is positioned adjacent to the desired tissue or structure to be ablated, the deployable segment of the treatment structure is extended away from the main catheter body and manipulated into one or more desired positions using the dedicated articulation mechanism. The deployable segment is manipulated within the imaging field by the clinician while receiving immediate feedback through a display of a conventional ultrasound console electrically coupled to the ultrasound transducer. Upon completion of the ablation therapy, the treatment structure articulation mechanism is operated to return the treatment structure to its non-deployed position and the catheter is removed from the body.

Significantly, the inclusion of the ultrasound imaging catheter and an independently-controllable treatment structure in a single catheter apparatus enables an administering clinician to quickly place all the elements necessary to perform a particular therapy in a desired location. In addition, restricting the range of movement of the treatment structure's therapeutic segment to a path that necessarily includes positions within the imaging field of the transducer enables the clinician to quickly and accurately determine the position of the therapeutic device. As a result of providing the image of both the therapeutic device and the surrounding anatomical features, the clinician may accurately perform and observe the application of the therapy and immediately monitor its results.

Further features and advantages of the present invention as well as the structure and operation of various embodiments of the present invention are described in detail below with reference to the accompanying drawings. In the drawings, like reference numerals indicate like or functionally similar elements. Additionally, the left-most one or two digits of a reference numeral identifies the drawing in which the reference numeral first appears.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

DETAILED DESCRIPTION

Figure 1A:
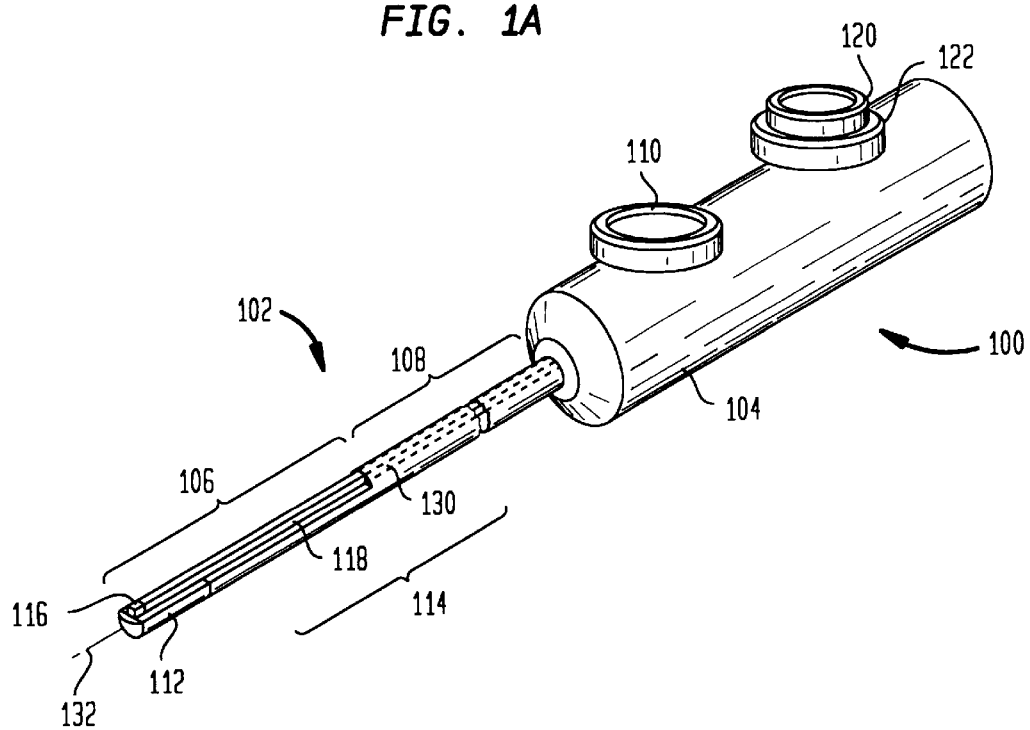
FIG. 1A is a perspective view of one embodiment of an ultrasound imaging and treatment catheter of the present invention having a side-mounted treatment structure.

A perspective view of one embodiment of the ultrasound imaging and treatment catheter apparatus 100 of the present invention is illustrated in FIG. 1A. The catheter apparatus 100 has a main catheter body 102 and a handle 104 for controlling the catheter body 102 during catheterization. The catheter body 102 is comprised of two primary segments: an operative segment 106 and a direction control segment 108. The operative segment 106 includes the primary functional elements of the catheter 100. The direction control segment 108 is connected to a control handle 104 at its proximal end and to the operative segment 106 at its distal end. Preferably, the direction control segment 108 is controlled by one or more articulation mechanisms 120, 122 on the control handle 104. The direction control segment 108 provides the necessary length to the main catheter body 102 such that the operative segment 106 can be positioned adjacent to a desired anatomical feature within the body. The main catheter body 102 has an ultrasound transducer 112 located proximate to its distal end. In accordance with one embodiment of the present invention, a treatment structure 114 is axially mounted to the main catheter body 102 and is independently controlled with an actuation mechanism 110. The treatment structure 114 includes a deployable segment 118 having a therapeutic segment 116 at or proximate to its distal end. A non-deployable segment 130 of the treatment structure 114 is connected to the handle 104 at its proximal end while the distal end of segment 130 is connected to the deployable segment 118. The non-deployable segment 130 is manipulated along with the direction control segment 108 of the main catheter body 102 and is shown in phantom in FIG. 1A.

Figure 1B:
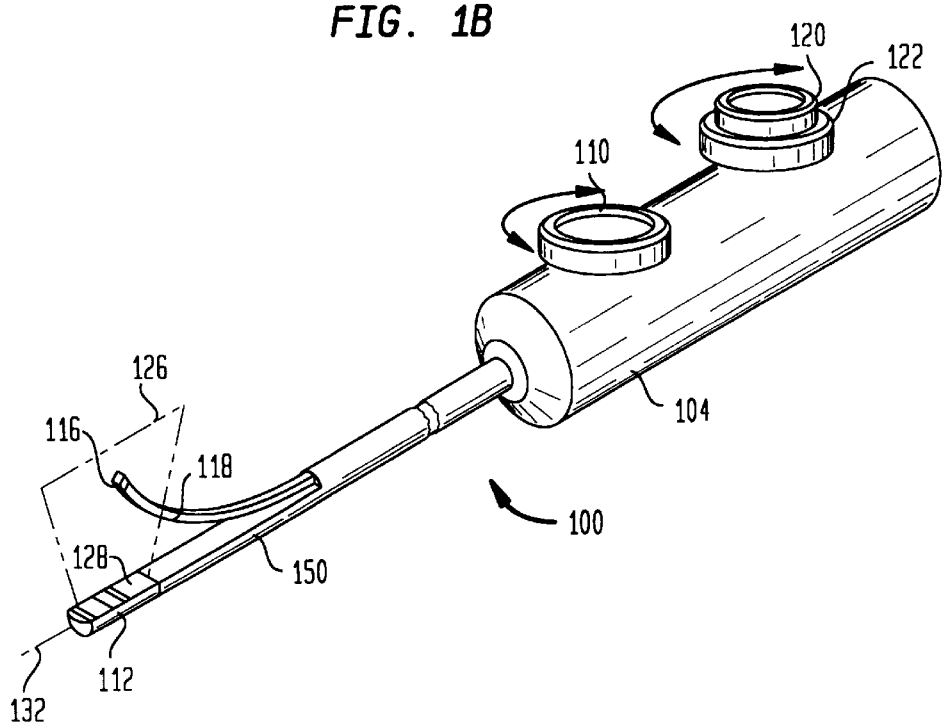
FIG. 1B is a perspective view of the catheter of FIG. 1A showing the therapeutic segment in a deployed position within an imaging field provided by an ultrasound transducer mounted in the catheter.

FIG. 1B shows the catheter apparatus 100 with the deployable segment 118 of the treatment structure 114 extended away from the main catheter body 102. In the illustrative embodiment, the imaging lens 128 of the ultrasound transducer 112 is positioned to provide a field of view 126 that is substantially orthogonal to the side of the catheter. Preferably, the field of view 126 is a substantially planar imaging field, although other configurations, such as a volumetric imaging field may be implemented in the present invention. All or a portion of the field of view 126 is included in a larger plane (not shown) that also includes longitudinal axis 132 of the main catheter body 102. The field of view 126 is on the same side of the main catheter body 102 as the treatment structure 114. Segment 118 of the treatment structure 114 is controlled independently of the main catheter body 102. As shown in FIG. 1A, in its retracted or non-deployed position, the segment 118 of the treatment structure 114 lies immediately adjacent to the main catheter body 102. In its extended or deployed position shown in FIG. 1B, the deployable segment 118 of the treatment structure 114 is curved away from the main catheter body 102, placing the therapeutic segment 116 at a desired location within the ultrasound imaging field 126.

In the illustrative embodiment shown in FIGS. 1A and 1B, the range of movement of the therapeutic segment 116 of the treatment structure 114 is restricted to locations within the ultrasound imaging field 126. Where the field is planar as shown in FIG. 1B, to insure that the active segment 116 does not laterally travel out of the imaging plane 126, the deployable segment 118 of the treatment structure 114 is configured to travel in a single plane in response to adjustments made through the articulation mechanism 110. As will be explained in greater detail below, the plane through which the deployable segment 118 travels includes the ultrasound imaging plane 126 since the treatment structure 114 is mounted on the same side of the main catheter body 102 as the imaging lens 128. Since the ultrasound transducer 112 provides a field of view that includes the surrounding anatomical features as well as the therapeutic segment 116, this novel arrangement insures that the administering clinician may quickly and accurately position the therapeutic segment 116 at an optimal position adjacent to a desired anatomical feature by deploying the therapeutic segment 116 to a location within the ultrasound imaging field 126.

In the illustrative embodiment shown in FIGS. 1A and 1B, the main catheter body 102 is controlled by one or more conventional articulation or steering mechanisms 120 and 122. Articulation mechanism 120 provides two-way horizontal steering of the main catheter body 102 while the articulation mechanism 122 provides two-way vertical steering. Together, the articulation mechanisms 120 and 122 provide four-way control of the main catheter body 102. Alternatively, the catheter apparatus 100 may have a single two-way steering control mechanism or none at all depending upon the application. It is noted that these articulating mechanisms 120 and 122 are distinct from the novel articulating mechanism 110 which provides independent two-way steering of the treatment structure 114. In the embodiment illustrated in FIGS. 1A and 1B, the treatment structure 114 travels towards and away from the catheter main body 102. As would be apparent to one skilled in the relevant art, articulation mechanisms 120 and 122 may be any conventional steering mechanisms such as those used in gastroscopes, endoscopes or in conventional catheter structures.

In the illustrative embodiment shown in FIG. 1B, the ultrasound imaging field 126 has a substantially planar, trapezoidal shape. As is well known in the art, phased array ultrasound transducers have a pie-shaped field of view, the apex of which is located at the center of the phased array. A linear array has a rectangular field of view with its vertical borders aligned with the edges of the transducer. Although the phased array ultrasound transducer provides far-field imaging, it does not provide sufficient near-field imaging due to its triangular shape. On the other hand, linear array transducers provide near-field imaging across the length of the array, but provide relatively narrow imaging in its far field. By controlling the center-most elements of the transducer 112 as a linear array and the end-most elements as a phased-array, the trapezoid-shaped imaging field 126 is achieved. As is well known in the art, in this embodiment, the ultrasound transducer 112 preferably has an element pitch that is sufficiently small so as to avoid constructive interference. Advantageously, this embodiment of the ultrasound transducer 112 provides sufficient resolution in both near and far fields, enabling the catheter apparatus 100 to be used to perform a wide variety of therapies. In alternative embodiments, the ultrasound transducer 112 comprises only phased array, linear array, or a linear array (CLA) elements, or some combination thereof, depending upon the desired application.

In one aspect of this embodiment of the present invention, catheter apparatus 100 is an intra-cardiac imaging and treatment catheter and the treatment structure 114 is referred to as an ablation support structure. The therapeutic segment 116 has an ablation electrode for performing cardiac ablation procedures under the guidance of ultrasound imaging provided by ultrasound transducer 112. In this aspect, the main catheter body 102 is configured to be positioned within the atrium or ventricle of the heart. The therapeutic segment 116 of the ablation support structure 114 is extended and retracted relative to the main body 102 through articulation mechanism 110 to place the ablation electrode adjacent to a desired cardiac structure or myocardium. As one skilled in the relevant art would find apparent, the therapeutic segment 116 may include any type of ablation electrode, such as an ablation electrode that generates direct current (DC), radio frequency (RF) or microwave energy. The ablation electrode may also be, for example, a laser or a cryoablation device. In addition, active segment 116 may include multiple ablation devices. For example, the active segment 116 may include a conduction block of 8, 10 or 12 ablation electrodes. In addition, the therapeutic segment 116 may include other therapeutic devices in addition to or instead of the ablation device. For example, therapeutic segment 116 may include appropriate devices for performing TMR (transmyocardial revascularization), chemical treatment of the heart, etc. In the latter application, the independently controllable treatment structure 114 also contains a channel along its length through which therapeutic chemicals are administered.

Regardless of the type of ablation or other therapeutic device incorporated in therapeutic segment 116, when the treatment structure 114 is deployed, the therapeutic segment 116 has a range of motion that includes locations that necessarily include locations only within the ultrasound imaging field 126. In the illustrative embodiment shown in FIGS. 1A and 1B, the therapeutic segment 116 has deployed and non-deployed positions which are both within the imaging field 126. The optimum range of the ultrasound imaging field 126 wherein the therapeutic segment 116 is clearly imaged may range from less than 1 centimeter to 7 or more centimeters, depending upon the type of ultrasound transducer 112 implemented and the anatomical feature to be treated. For example, in the intra-cardiac imaging and treatment catheter embodiment of the present invention, when ablating the right atrium, the near-to-mid-field (0.5–4.0 centimeters from the imaging lens 128) may be the optimal portion of imaging field 126. On the other hand, when viewing the left ventricle, the mid-to-far-field (2.0–8.0 centimeters) may be more desirable. Significantly, the ablation electrode 116 may be quickly and accurately positioned to these desirable locations simply by manipulating the articulation mechanism 110. Advantageously, by restricting the path of the therapeutic segment 116 to include locations within the ultrasound imaging field 126, the administering clinician does not have to use additional imaging techniques to locate separate catheters, nor does the clinician have to use the ultrasound transducer to search for the ablation electrode prior to performing the ablation therapy.

Figure 2A:
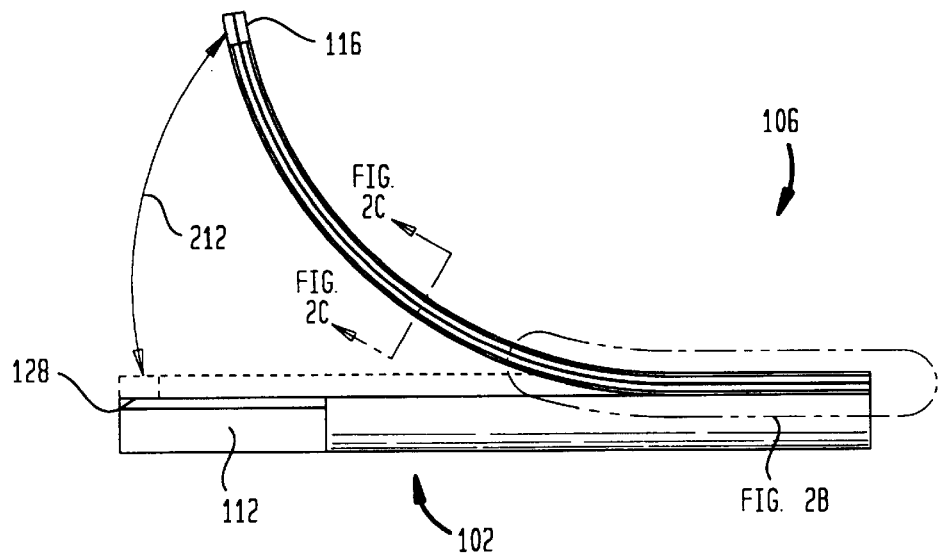
FIG. 2A is an exposed view of the treatment structure of the catheter illustrated in FIGS. 1A and 1B.
Figure 2B:
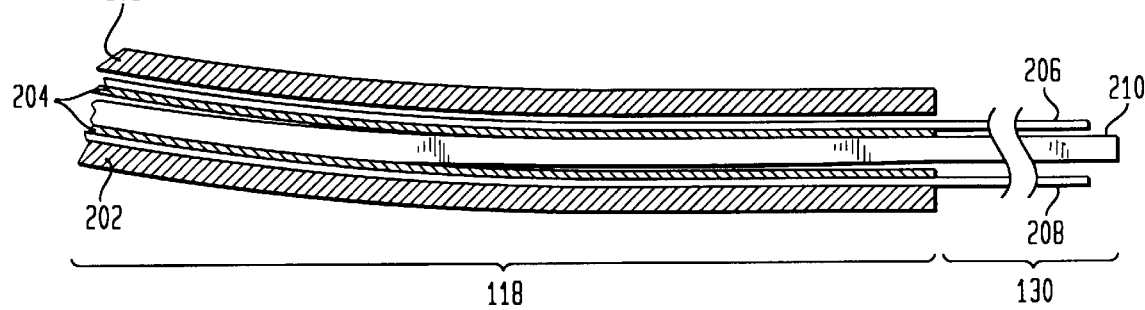
FIG. 2B is a cross-sectional view of the treatment structure of the catheter illustrated in FIGS. 1A and 1B taken along its longitudinal axis.
Figure 2C:
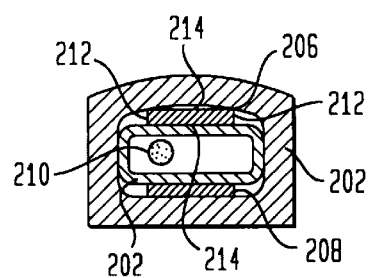
FIG. 2C is a cross-sectional view of the deployable segment of the treatment structure of the catheter illustrated in FIGS. 1A and 1B taken along lines 2C—2C of FIG. 2A.

The internal structure of the treatment structure 114 shown in FIGS. 1A and 1B will now be described with reference to FIGS. 2A–2C. FIG. 2A is a schematic diagram of the operative segment 106 showing the deployable segment 118 of the treatment structure 114 in its deployed position. FIG. 2B is a cross-sectional view of the treatment structure 114 taken along its longitudinal axis 132. FIG. 2C is a cross-sectional view of the treatment structure 114 taken along section lines 2C–2C of FIG. 2A at its deployable segment 118.

Referring to FIGS. 2A–2C, the treatment structure 114 includes upper deflection band 206 and lower deflection band 208, each of which extends axially along the deployable segment 118. Deflection bands 206 and 208 are slidingly positioned between flexible outer sleeve 202 and flexible inner sleeve 204. The deflection bands 206 and 208 are connected in a known manner to the articulation mechanism 110 in the catheter handle 104, preferably with flexible, high-strength cables (not shown) contained in the non-deployed segment 130. Articulation mechanism 110 may be any well known articulation mechanism. For example, articulation mechanism 110 may be a rotational steering mechanism that releases one cable while simultaneously retracting the other cable. In such an embodiment, when the articulation mechanism 110 is rotated in one direction, a tensile force is applied to the proximal end of the upper deflection band 206 due to the retraction of its associate cable, while the lower deflection band 208 is extended due to the release of its associated cable. This causes the deployable segment 118 to extend away from the main catheter body 102. In like manner, rotation of the articulation mechanism 110 in an opposite direction causes the deployable segment 118 to retract toward the main catheter body 102.

The deflection bands 206 and 208 have a variable stiffness along their length. Specifically, the deflection bands 206 and 208 have less stiffness along deployable segment 118 and a greater stiffness along the non-deployable segment 130. As a result, the deflection bands 206 and 208 will cause the treatment structure 114 to bend only along its deployable segment in response to an applied tensile force as described above. This insures that the treatment structure 114 responds predictably to an applied tensile force. This in turn insures that the therapeutic segment 116 will travel in a predictable and predetermined path 212 as the treatment structure 114 is extended and retracted.

As shown in FIG. 2C, the deflection bands 206 and 208 preferably have a rectangular cross-section, with substantially parallel short sides 212 that are considerably longer than the adjacent long sides 214 which are substantially parallel to each other and to the imaging lens 128 of the transducer 112. In addition, the long sides 214 of the rectangular deflection bands 206 and 208 are in a plane that includes the imaging lens 128 and the longitudinal axis 132. This rectangular cross-section restricts the direction or angle at which the deflection bands 206 and 208 bend in response to applied tensile forces. In the illustrative embodiment where the imaging field 126 is substantially planar, to insure that the bending of the treatment structure 114 occurs only in the plane that necessarily includes locations only within the planar imaging field 126, the deflection bands 206 and 208 each have a greater stiffness in a plane including the short sides 212 than in the plane that includes the long sides 214 of the rectangular deflection bands 206 and 208. Thus, in this embodiment, the treatment structure 114 travels directly away from and towards the side of the main catheter body 102 from which the planar imaging field 126 is projected. That is, the treatment structure 114 bends along the deployable segment 118 in a single plane away from and towards the catheter main body 102 in response to tensile forces applied to the proximal ends of the deflection bands 206 and 208, placing the therapeutic segment 116 in a desired location within the imaging field 126.

The catheter of the present invention can be utilized in a medical system including the appropriate control circuitry for controlling the operation of the ultrasound transducer. The control circuitry is electrically connected to a transceiver circuitry for receiving and transmitting signals via a cable to the ultrasound transducer. In turn, the transceiver circuitry is electrically interconnected to suitable imaging circuitry which is connected to a display for displaying ultrasound images. As shown in FIGS. 2B and 2C, a treatment connection lead 210 extends within the interior of the treatment structure 114 between deflection bands 206 and 208. The treatment connection lead 210 electrically couples the therapeutic device, such as an ablation electrode located in therapeutic segment 116 with control and display circuitry not shown.

Figure 3A:
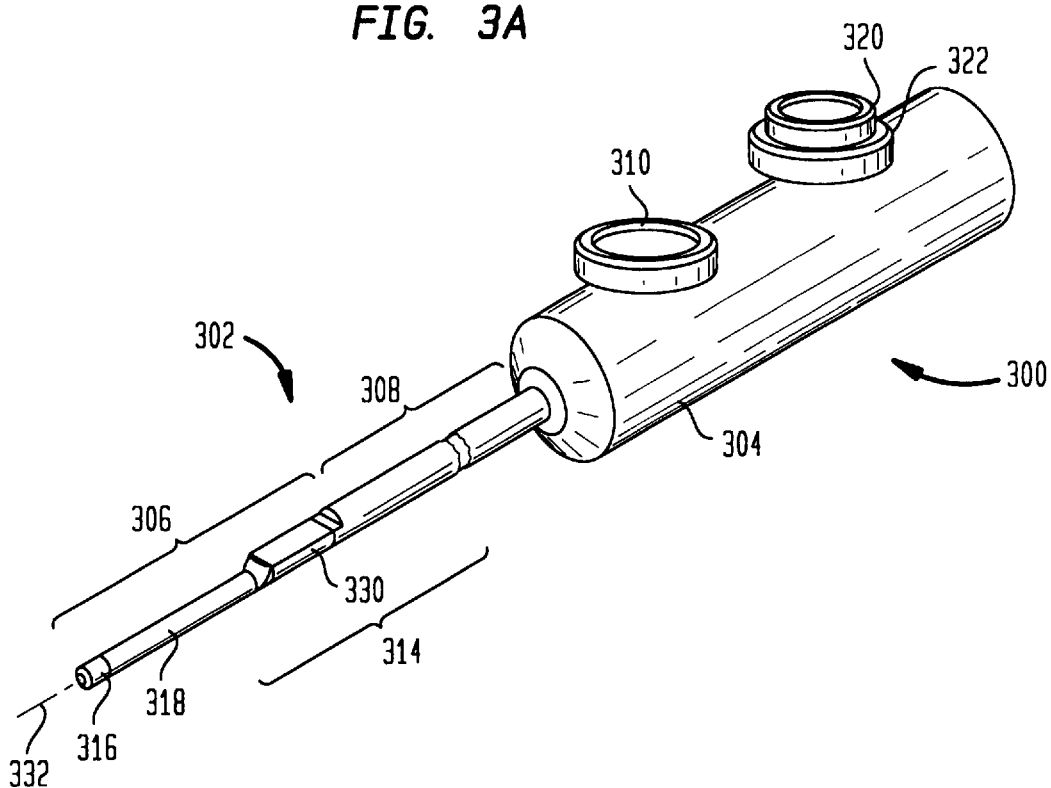
FIG. 3A is a perspective view of another embodiment of the ultrasound imaging and treatment catheter of the present invention having a tip-mounted treatment structure.

A perspective view of another embodiment of imaging catheter apparatus 300 having a tip-mounted treatment structure is illustrated in FIG. 3A. The catheter apparatus 300 has a main catheter body 302 and a control handle 304 for controlling the catheter 302 during catheterization. The main catheter body 302 is comprised of two primary segments: An operative segment 306 including the primary functional elements of the catheter 300; and a direction control segment 308 connected to and preferably controlled by articulation mechanisms 320 and 322 of the control handle 304.

The main catheter body 302 has a treatment structure 314 mounted axially along the length of the main catheter body 302. The treatment structure 314 is independently controlled with actuation mechanism 310. The treatment structure 314 includes a deployable segment 318 having an therapeutic segment 316 at or proximate to its distal end. A non-deployable segment 330 of the treatment structure 314 includes the ultrasound transducer 312 and is manipulated only with the direction control segment 308 of the main catheter body. The ultrasound transducer 312 is located at the proximal end of the operative segment 306 rather than towards its distal end as in catheter 100.

As in the catheter 100, the direction control segment 308 provides the necessary length to the main catheter body 302 such that the operative segment 306 can be positioned adjacent to a desired anatomical feature within the body. However, unlike catheter 100, the operative segment 306 and the treatment structure 314 are essentially the same. That is, in the catheter 100, the operative segment 106 includes the deployable segment 118 of the treatment structure 114 and a portion 150 of the main catheter body 102 that remains stationary during deployment of the treatment structure 114. In the catheter 300, the transducer 312 is located in a non-deployable segment 330 of the treatment structure 314 that remains stationary during deployment of the treatment structure 314; there is no other portion of the operative segment 306 that remains stationary. Thus, the operative segment 306 of the catheter 300 essentially includes only the treatment structure 314 of the present invention, which includes a deployable segment 318 and a non-deployable segment 330.

Figure 3B:
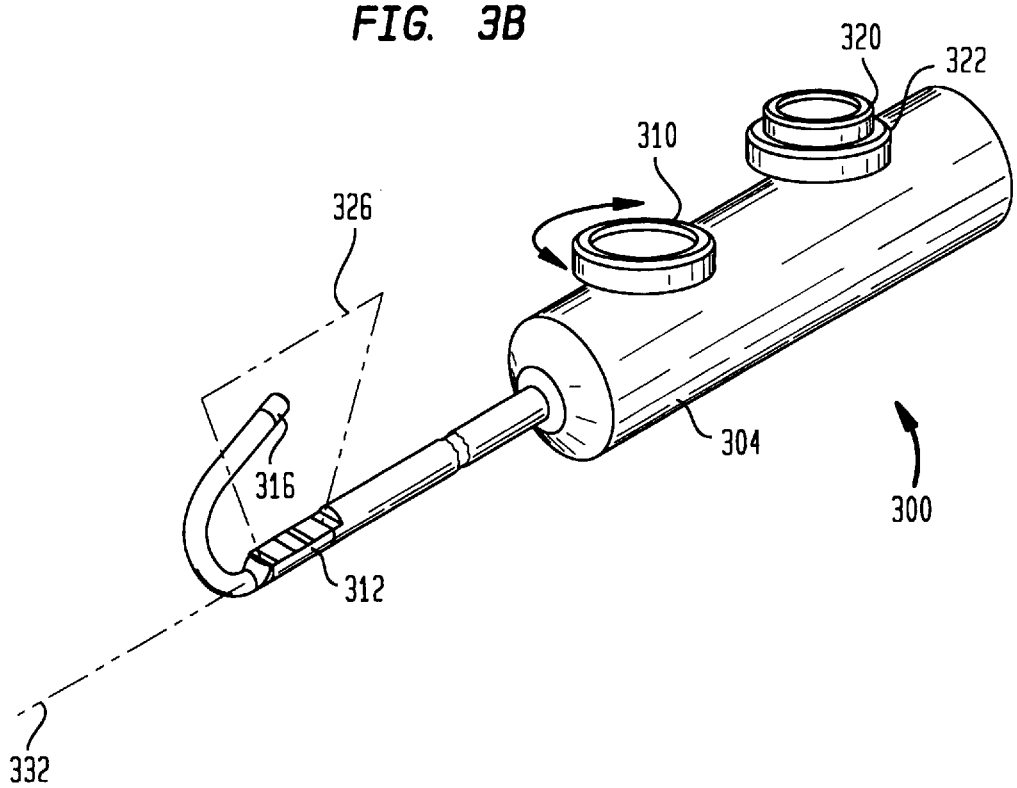
FIG. 3B is a perspective view of the catheter of FIG. 3A with the therapeutic segment in its deployed position within the imaging field.

As shown in FIG. 3A, in its retracted or non-deployed position, the treatment structure 314 is aligned with the longitudinal axis 332. FIG. 3B shows deployed segment 318 of the treatment catheter 314 extended back towards the handle 304 in a deployed position. The imaging lens 328 of the ultrasound transducer 312 is positioned to provide a field of view 326. As described below with reference to FIGS. 4A–4C, the imaging field 326 and the treatment structure 314 are positioned such that when the treatment structure 314 is deployed, therapeutic segment 316 travels in a predetermined path that necessarily includes positions within the ultrasound imaging field 326. As with catheter 100, the treatment structure 314 is controlled independently of the main catheter body 302 through an articulating mechanism 310.

It is noted that in the embodiment illustrated in FIGS. 1 and 2, the active segment 116 travels between an unfocused non-deployable position to one of many focused deployed positions within the imagining field 126. In the embodiment shown in FIGS. 3 and 4, the active segment 316 travels from a position outside the imaging field 326 to a desired location within the imaging field 326 when it is deployed. Thus, in accordance with the present invention, the range of movement of the active segment 316 of the treatment structure 314 is not restricted to locations within the ultrasound imaging field 326 when in its non-deployed position. However, the range of movement of the active segment 316 is restricted to locations that necessarily include locations within the ultrasound imaging field 326. As with catheter 100, the therapeutic segment 316 is configured to travel in a predetermined path that includes locations within the ultrasound imaging field of view 326. By manipulating the deployable segment 318 to position the therapeutic segment 316 at a location within the ultrasound imaging field 326 where it is clearly imaged enables the administering clinician to quickly and accurately position the therapeutic segment 316 at a desired location adjacent to an anatomical feature also visible within the imaging field 326.

The main catheter body 302 may be controlled by one or more conventional articulation or steering mechanisms 320 and 322 as described above. These articulating mechanisms 320 and 322 are distinct from the articulating mechanism 310 of the present invention providing two-way steering of the treatment structure 314 relative to the catheter main body 302.

Figure 4A:
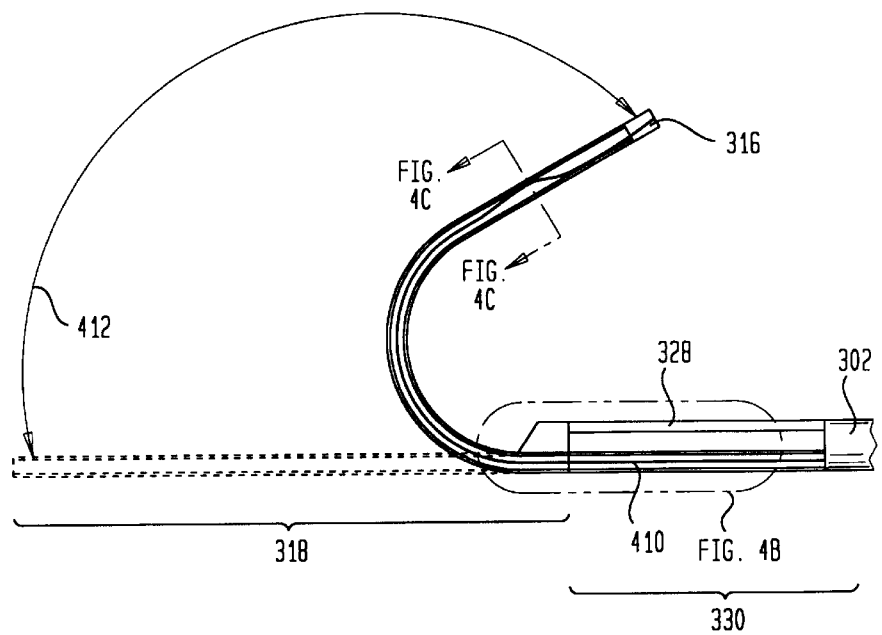
FIG. 4A is an exposed view of the treatment structure of the catheter illustrated in FIGS. 3A and 3B.
Figure 4B:
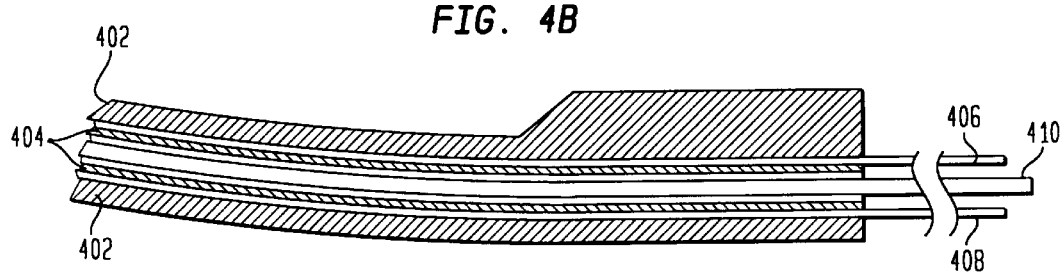
FIG. 4B is a cross-sectional view of the treatment structure of the catheter illustrated in FIGS. 3A and 3B taken along its longitudinal axis.
Figure 4C:
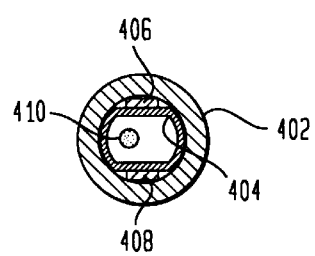
FIG. 4C is a cross-sectional view of the deployable segment of the treatment structure of the catheter illustrated in FIGS. 3A and 3B taken along lines 4C—4C of FIG. 4A.

The internal structure of the treatment structure 314 of the present invention will now be described with reference to FIGS. 4A–4C. FIG. 4A is a schematic diagram of the operative segment 306 showing the deployable segment 318 of the treatment structure 314 in its deployed position. FIG. 4B is a cross-sectional view of the treatment structure 314 taken along the longitudinal axis 332. FIG. 4C is a cross-sectional view of the treatment structure 314 of the present invention taken along section lines 4C—4C of FIG. 4A at its deployable segment 318 and orthogonal to the longitudinal axis 332.

Referring to FIGS. 4B and 4C, the treatment structure 314 includes upper deflection band 406 and lower deflection band 408, each of which extend axially along its deployable segment 318. Deflection bands 406 and 408 are slidingly positioned between flexible outer sleeve 402 and flexible inner sleeve 404. The deflection bands 406 and 408 are connected to articulation mechanism 310 in the catheter handle 304 with flexible, high-strength cables (not shown) contained in the main catheter body 302. The bands 404 and 406 have similar configurations and composition and respond in a similar manner to applied tensile forces as deflection bands 204 and 206 described above with reference to catheter 100.

During operation, the treatment structures 114/314 are placed in their non-deployed position as shown in FIGS. 1A and 3A. The catheter is then inserted into the body until the distal end of the catheter is at a desired location. The treatment structure is then deployed such that the therapeutic segment, 116/316 of the treatment structure is at a desired location within the ultrasound imaging field 126/326. The therapeutic treatment is then performed under ultrasonic guidance and, upon completion, the treatment structure is returned to its non-deployed position. When inserted into the body, the main catheter body 102/302 may be controlled by one or more articulation mechanisms 120/320 and 122/322. Adjustments of these articulation mechanisms change the direction of direction control segments 108/308 causing the operative segments 106/306 to likewise change direction.

While various embodiments of the present invention have been described above, it should be understood that they have been presented by way of example only, and not limitation. Thus, the breadth and scope of the present invention are not limited by any of the above-described exemplary embodiments, but are defined only in accordance with the following claims and their equivalents.

What is claimed is:

1. A catheter comprising:
   an elongate flexible main catheter body having proximal and distal ends;
   an ultrasound transducer, fixedly coupled to said main catheter body and configured to provide a field of view; and
   an elongate treatment structure having a deployable segment with a proximate end fixed to said main catheter body and a therapeutic device at its distal end, said deployable segment configured to have a restricted and predetermined range of motion controllable independently of said main catheter body, resulting in said therapeutic device traveling in a predetermined path that confines all operative positions to be within said field of view.

2. The catheter of claim 1, wherein said non-deployable segment has proximal and distal ends, and is axially secured to said main body, wherein said deployable segment has a proximal end connected to said distal end of said non-deployable segment.

3. The catheter of claim 2, wherein said treatment structure further comprises:
upper and lower deflection bands axially extending through said deployable segment, said deflection bands configured to restrict said deployable segment to said restricted range of motion.

4. The catheter of claim 3, wherein said treatment structure further comprises:
inner and outer flexible sleeves axially extending along said deployable segment and encompassing said upper and lower deflection bands.

5. The catheter of claim 3, wherein said upper and lower deflection bands have a first stiffness in said deployable segment and a second stiffness in said non-deployable segment that is greater than said first stiffness.

6. The catheter of claim 3, wherein said upper and lower deflection bands have a rectangular cross-section with substantially parallel first sides and substantially parallel second sides substantially shorter than said first sides, said first sides of said deflection bands located in said common plane.

7. The catheter of claim 2, further comprising:
a handle connected to said proximal end of said main catheter body and said proximal end of said treatment structure; and
an articulation mechanism, mounted in said handle, configured to control said treatment structure independently of said main catheter body.

8. The catheter of claim 2, wherein the catheter is a cardiac imaging and ablation catheter; and wherein
said main catheter body is configured to be positioned within the atrium and ventricle of the heart; and wherein
said treatment structure is an ablation support structure having one or more ablation electrodes at said therapeutic device.

9. The catheter of claim 1, wherein said ultrasound transducer comprises linear array elements.

10. A catheter apparatus comprising:
an elongate flexible main catheter body having proximal and distal ends;
an ultrasound transducer, integrated into a first side of said main body proximate to said distal end, configured to provide a field of view within an imaging field substantially orthogonal to said first side of said main catheter body; and
an elongate flexible treatment structure, axially fixed on said first side of said main catheter body and having proximal and distal ends, including, a therapeutic device at said distal end of said treatment structure,
wherein motion of said treatment structure is controllable independently of said catheter main body such that said treatment structure is extended away from and retracted towards said main catheter body to provide said therapeutic device with a range of movement that confines all operative locations to be within said imaging field.

11. The catheter of claim 10, wherein said treatment structure further comprises:
a non-deployable segment, integral with said main body, having proximal and distal ends;
a deployable segment, having a proximal end connected to said distal end of said non-deployable segment, and a distal end including said therapeutic device; and
upper and lower deflection bands interposed between said inner and outer sleeves and axially extending through said deployable and non-deployable segments, said deflection bands configured to bend so as to restrict said extension and retraction of said deployable segment to a predetermined path having positions within said imaging field.

12. The catheter of claim 11, wherein said upper and lower deflection bands have a first stiffness in said deployable segment and a second stiffness greater than said first stiffness in said non-deployable segment.

13. The catheter of claim 11, further comprising:
inner and outer flexible sleeves axially extending along said deployable segment and surrounding said upper and lower deflection bands.

14. The catheter of claim 11, wherein the catheter is a cardiac imaging and ablation catheter; wherein
said main catheter body is configured to be positioned within an atrium and ventricle of a heart; and wherein
said treatment structure is an ablation support structure with one or more ablation electrodes at said active segment.

15. The catheter of claim 14, wherein said ablation electrode generates radio frequency energy.

16. The catheter of claim 14, wherein said ablation electrode generates microwave energy.

17. The catheter of claim 11, wherein said ultrasound transducer comprises linear array elements.

18. A cardiac imaging and ablation catheter apparatus comprising:
an elongate flexible main catheter body having proximal and distal ends and configured to be positioned within an atrium and ventricle of a heart;
an ultrasound transducer, mounted into a side of said main body proximate to said distal end, configured to provide a field of view within a imaging field substantially orthogonal to said side of said main catheter body; and
an elongate flexible ablation support structure, axially fixed on said side of the main catheter body and having proximal and distal ends, including,
a deployable segment, having proximal and distal ends, configured to be positioned in a non-deployed position and a range of deployed positions, including an ablation electrode with a range of movement restricted to a predetermined path necessarily including operative locations within said imaging field when said deployable segment travels through said range of deployed positions,
a non-deployable segment, having a distal end connected to said proximal end of said deployable segment and a distal end, axially coupled to said main catheter body;
inner and outer flexible sleeves extending axially along said deployable segment, and
upper and lower deflection bands interposed between said inner and outer sleeves and axially extending through said deployable segment, said deflection bands configured to restrict said deployable segment to said range of deployed positions.

19. The catheter of claim 18, wherein said upper and lower deflection bands have a composition such that said bands are more bendable in said deployable segment than in said non-deployable segment.

20. The catheter of claim 18, further comprising:
a handle connected to said proximal end of said main catheter body and said ablation support structure; and an articulation mechanism, mounted in said handle, configured to control said ablation support structure.

21. The catheter of claim 18, wherein said ablation electrode generates radio frequency energy.

22. A method for performing cardiac imaging and ablation, comprising the steps of:
1) articulating an elongate flexible main catheter body having proximal and distal ends so that said distal end is positioned within a desired location within a body;
2) manipulating, through an independent control means that does not control said main catheter body, an elongate flexible ablation support structure from a non-deployed position wherein an axis of said elongate support structure is substantially parallel with a longitudinal axis of said main catheter body, to one of a plurality of deployed positions that necessarily requires said ablation electrode to have operative positions within a field of view of an ultrasound transducer mounted within said main body;
3) performing the ablation therapy under guidance of said ultrasound transducer; and
4) retracting said ablation support structure to said non-deployed position.

* * * * *